United States Patent [19]

Leung

[11] Patent Number: 5,304,574

[45] Date of Patent: Apr. 19, 1994

[54] METHODS OF TREATMENT OF CLINICAL CONDITIONS USING PANTOTHENIC ACID

[76] Inventor: Lit-Hung Leung, Room 502, Dragon Seed Building, 39 Queen's Road Central, Hong Kong, Hong Kong

[21] Appl. No.: 927,189

[22] Filed: Aug. 7, 1992

Related U.S. Application Data

[63] Continuation of Ser. No. 713,965, Jun. 11, 1991, abandoned.

[30] Foreign Application Priority Data

Feb. 11, 1991 [GB] United Kingdom ............... 9102830

[51] Int. Cl.⁵ .................... A01N 37/12; A01N 37/44; A61K 31/195
[52] U.S. Cl. .................................................. 514/563
[58] Field of Search ........................................ 514/563

[56] References Cited

U.S. PATENT DOCUMENTS 4,619,829 7/1986 Motschan ..................... 514/251

FOREIGN PATENT DOCUMENTS 1033843 6/1966 United Kingdom .

OTHER PUBLICATIONS

Early et al., Int. Z. Angow. Physiol. 27, 43–50 (1969).
Smith et al., Metabolism, vol. 36, Feb. 2, 1987, pp. 115–121.
Hackh's Chemical Dictionary, McGraw Hill, U.S.A., 1969, pp. 713–714.
Eddy, Vitaminology, Williams and Williams, Baltimore, 1949, pp. 194–197.
Sebrill et al., The Vitamins, Academic Press, N.Y., 1954, pp. 649–679.

*Primary Examiner*—Marianne M. Cintins
*Assistant Examiner*—Rebecca Cook
*Attorney, Agent, or Firm*—Thompson, Hine and Flory

[57] ABSTRACT

A method for treating human beings suffering from chronic bronchial asthma, acute rhinitis, disseminated lupus erythematosus, or neurodermatitis which comprises administering to said human being a therapeutically effective amount of pantothenic acid or a derivative.

7 Claims, No Drawings

METHODS OF TREATMENT OF CLINICAL CONDITIONS USING PANTOTHENIC ACID

This is a continuation of co-pending application Ser. No. 07/713,965, filed Jun. 11, 1991, now abandoned.

FIELD OF THE INVENTION

This invention relates to the treatment of individuals in steroid therapy wherein pantothenic acid or a derivative thereof which is converted to pantothenic acid in the body is administered to the individual in place of the steroids. Substitution of the pantothenic acid or derivative thereof for steroids not only retains all of the usefulness of the steroids, but, at the same time, it avoids all of the undesirable effects that go along with chronic steroid therapy.

BACKGROUND OF THE INVENTION

The androgens are responsible for the primary and secondary sexual characteristics in the male. Among their many other functions, the androgens have a strong anabolic effect on protein metabolism with pronounced muscular development and increased muscular strength. It also imparts a general feeling of well-being to the individual.

Scientists and medical researchers took advantage of these particular features of the androgens, and began in the 1950's experimenting with the androgenic-anabolic steroids, which are the synthetic analogues of the male hormone testosterone, the main androgen n the body, with a view to improve muscle strength and, at the same time, to avoid all the androgenic side effects, especially the virilizing and masculinizing effects in the female. However, it is impossible to dissociate the anabolic effect from the androgenic side effect in all the synthetic androgenic-anabolic steroids. Despite this fact, many athletes have little hesitation in taking the androgenic-anabolic steroids in order to achieve a winning edge over their competitors. The use of this group of drugs is approaching epidemic proportions, and many athletes are beginning to use these drugs as early as their high school days.

At the present time, the use of androgenic-anabolic steroids in athletes is still very controversial, and is not recommended by the medical profession for two reasons. Firstly, it is still uncertain whether these steroids do in fact improve athletic performance. Secondly, and more important, it is still to be determined to what extent these drugs may be harmful to the athletes.

There are conflicting reports relating to the efficacy of the androgenic-anabolic steroids in improving athletic performance. While there are many studies suggesting that these steroids do not improve athletic performance, many athletes are convinced that these steroids not only enhance their athletic performance, but also convey a general sense of well-being to the individual. This sense of well-being allows them to fit into a tighter practice schedule, thus enhancing their performances. There are also reports suggesting that these steroids are responsible for many of the record-breaking performances. The controversy relating to the use of the androgen-anabolic steroids goes a step further because of the potential risks involved, especially when these drugs are administered on a long term basis.

Briefly, suspected side effects of the androgenic-anabolic steroids include various hepatic abnormalities (for example, abnormal liver function tests, intrahepatic structural changes, malignant liver tumors, etc.), changes in cardiovascular risk factors with a change in lipoprotein cholesterol level and hypertension, endocrinology effects (for example, sterility, testicular atrophy and gynaecomastia in the male and masculinization, disturbances in the menstrual period, virilization including hirsutism and deepening of the voice in the female) and psychological changes including mood changes and changes in libido.

Present evidences suggest that many of the side effects of the androgenic-anabolic steroids are reversible once the drugs are discontinued. However, the side effects after long term administration, especially if high dosages are taken, are not so clear. Serious side effects, like hepatomas, though rare, can be rapidly fatal and are especially worrying. This is enough to alarm the scientific and medical world to impose a ban on the use of these steroids in competitive sports.

The reason why administration of these androgenic-anabolic steroids leads to such untoward effects is not known. A close parallel is the administration of estrogens in the female with the danger of developing cervical cancers and other adverse effects. A possible explanation is that the administration of exogenous hormones tends to upset the homeostasis of the body system, and such derangement eventually leads to the development of such side effects.

It is interesting to note that, in the body, the androgens in fact include a number of similar and related compounds, and so are the estrogens. But it is not known why nature should decide that such an arrangement should be necessary, since their functions in the body are very similar. A possible answer is that it is related to the feedback mechanism of the androgens to the gonadotropic function of the pituitary, whose true nature is still not completely known to medical science. Administration of a single androgen may therefore upset the delicate balance of the others, resulting in a derangement of the homeostasis of the body, with the consequence of developing the adverse effects.

It is also known that the plasma androgen level varies through a wide range of about 0.2 to 1 microgram per dl in the normal males. The reason why a relatively high level of natural androgens in the body will not produce any side effects is probably due to the fact that the relative proportions of the different androgens are well balanced, being regulated by the autoregulatory functions of the body in a very refined and delicate manner, so that the feedback mechanism to the pituitary is not disturbed.

If the range of the normal androgen level is so wide, maybe it is appropriate to know the optimum androgen level in the body; or, indeed, whether the optimum level is ever reached in a normal individual. It seems certain that the optimum level varies in different individuals. As to whether an optimum level of androgen is reached in normal individuals, there are evidences to show that it is not. For example, most athletes believe that administration of androgens will improve their strength and performance, together with an increase in muscle bulk, though this increase in muscle bulk is much less than in the replacement therapy with androgens in patients with hypogonadism. And one possible conclusion that can be drawn from this particular observation is that while there is a definite deficiency of androgens in hypogonadism, it may also be possible that there is a relative deficiency of androgens in many seemingly normal individuals. Otherwise, there is no good reason why administration of additional androgens will lead to further increase in the muscle bulk.

The above description and reasoning suggest strongly that there is a certain degree of deficiency of androgens in most seemingly normal individuals. But to make up the deficiency by administering exogenous androgens, especially over a prolonged period of time, will necessarily lead to adverse effects due to the disturbance of the homeostasis and the feedback mechanism, as explained above. This is a tricky situation and the solution cannot be found easily.

It is clear from the above argument that side effects will not and cannot be avoided as long as exogenous steroids are administered. The only apparent solution is to depend on the auto-regulatory system of the body to synthesize the optimum level of the androgens as is required for a particular individual, so that the body can function at its best.

As explained in copending patent application U.S. Ser. No. 07/580,019 relating to the treatment of acne vulgaris, at least 90% of the population will develop acne vulgaris sometime in their life. The development of acne vulgaris is indicative that there is a deficiency of pantothenic acid in the form of acetyl-CoA. Due to the complexity of the body functions, the absence of acne vulgaris in the 10% does not necessarily mean that there is no deficiency in pantothenic acid, only that the deficiency may present itself in other forms. Thus, it seems that most people, if not all, will have some form of deficiency of pantothenic acid in the form of acetyl-CoA. All steroidal compounds are synthesized from acetate units in the form of acetyl-CoA, so that a deficiency in acetyl-CoA will necessarily affect the synthesis of the sex hormones, be it the androgens or the estrogens, and the level of these hormones will not be at their optimum level. In accordance with the present invention, administering pantothenic acid as a replacement for steroidal compounds will help to reverse the situation completely. Through the auto-regulatory function of the body, all the steroidal hormones will be synthesized to their optimum level, and the desired optimum level of the androgens are achieved, resulting in the best anabolic effect possible without any of the side effects being experienced. The ideal situation is thus achieved.

As another aspect of this invention, steroids are widely used in a great variety of clinical conditions to alleviate symptoms of various diseases. Steroids, in this context, include all the corticosteroids secreted by the adrenal cortex and all the synthetic steroid analogues of cortisol with similar actions. However, aside from their use as replacement therapy, in situations where the body fails to secrete an adequate amount of natural steroids, the use of synthetic steroids in clinical practice is empirical. The mechanism is never adequately explained, and their use is never curative in the sense that it is not directed towards the etiology of the disease process, but is merely palliative. The use of steroids has the added disadvantage in producing a lot of very grave undesirable effects, particularly when used on a long term basis, though a short course of a few days is unlikely to produce any serious side effects. Despite the undesirable effects, steroids are powerful drugs in symptomatic treatment, so that in many instances their use is reserved as a last resort when all other forms of medical treatment fails. To minimize the side effects, the dosage prescribed is always kept to the minimum.

Goodman and Gilman, *The Pharmacological Basis of Therapeutics*, Sixth Edition, Macmilan Publishing Co., Inc., p. 1489–1492, presents a brief outline of important uses of steroids in clinical practice for the treatment of various clinical conditions or diseases as set out below.

Rheumatism and arthritis, particularly rheumatoid arthritis and osteoarthritis.

Rheumatic carditis.

Some form of nephrotic syndrome attributable to systemic lupus erythematous.

The group of diseases called collagen diseases or connective tissue diseases.

Allergic diseases such as hay fever, serum sickness, urticaria, contact dermatitis, drug reactions, bee stings, angioneurotic edema and anaphylaxis.

Bronchial asthma, particularly chronic bronchial asthma.

Some forms of ocular diseases. Mainly used topically for diseases of the outer eye and anterior chamber. Posterior chamber diseases require systemic administration.

Skin diseases. Maibach and Stoughton have divided 20 dermatological disorders that respond to topical corticosteroids (see, Topical Corticosteroids, *Med. Clin. North Am.*, 1973, vol. 57, 227–233.)

Some forms of diseases of the intestinal tract, e.g., celiac sprue, and crohn's disease.

Cerebral edema that is associated with tumors.

Some forms of malignancies, e.g., lymphomas, acute lymphocytic leukemia, carcinoma of the breast and in combination chemotherapy in association with alkylating agents such as cyclophosphamide.

Some forms of liver diseases, e.g., various types of hepatitis and cirrhosis.

Miscellaneous Diseases including sarcoidosis, thrombocytopenia, hemolytic anemias and organ transplantation.

In all these conditions, the use of steroids is entirely empirical, and even if the dosage is kept to the minimum, over a prolonged period of time, the side effect is still considerable. The more significant side effects can be summed up as follows:

Suppression of pituitary-adrenal function.

Fluid and electrolyte disturbances.

Hyperglycemia and glycosuria.

Increased susceptibility to infections.

Bleeding or perforated peptic ulcers.

Osteoporosis.

A characteristic myopathy.

Behavioral disturbances.

Posterior subcapsular cataracts.

Arrest of growth.

Cushing's habitus, consisting of "moon face", "buffalo hump", enlargement of supraclavicular fat pad, "central obesity", striae, ecchymoses, acne, and hirsutism.

Since steroid treatment is empirical, one very pertinent question is whether the action of the steroids is indeed due to the steroids themselves. This question is not odd and seems all the more reasonable since the range of action of steroids is so wide, from arthritis to allergy, from connective tissue diseases to asthma, from skin disorders to inflammatory diseases and others. It is not only amazing but intriguing and there are few other drugs having a similar wide range of action. With such a wide range of action, it is unlikely that it will act through certain target receptors, and some other explanations must be sought.

It is postulated that the action of the administered steroids in all these disease processes is not exerted through the steroids themselves, but that these administered steroids are in fact only sparing the raw material for steroid synthesis, and that it is the raw material for steroid synthesis that is actually doing the healing work. As is known, the steroids are synthesized from units of acetates derived from acetyl-Co A. And it is the acetyl-Co A, or rather, Coenzyme A, that is doing all the healing work. Coenzyme A is unique among all the coenzymes of the body in that it is the only coenzyme to stand in the crossroad of the final common pathway of carbohydrate, fat and protein metabolism, and is the key precursor in the synthesis of many different lipids. And the significance of Coenzyme A in lipid synthesis is even more impressive when it is known that most cell membranes contain about 40% of lipid, and that cholesterol, the precursor of fecal sterols, bile acids, and the steroid hormones, is synthesized from units of acetate derived from acetyl-Co A. A deficiency in Coenzyme A thus has the potential of extensively affecting the biochemical reactions in the body, depending on other concommitant conditions.

Steroids are peculiar in the sense that they are not stored in the body, so that they have to be synthesized almost continuously. And steroids are also essential for survival. For these two reasons, the steroids have to be synthesized continuously, under any condition, even when the body is deficient in acetyl-Co A, which, for practical purposes, is equivalent to a deficiency in Coenzyme A. This means that steroid synthesis has the privilege of claiming priority for units of acetyl-Co A in case of shortage at the dispense of other biochemical reactions, even though the derangement of these other biochemical reactions will, in the long run, lead to other forms of illnesses, which may be fatal. The body is concerned with the immediate survival rather than the distant future, and these reactions are sacrificed in preference to steroid synthesis.

As has been explained in copending U.S. patent application Ser. No. 07/580,019, now U.S. Pat. No. 5,039,698, a deficiency in Coenzyme A through a deficiency in pantothenic acid is very common. In such a deficiency state, all the metabolic processes that go through the crossroad of the final common metabolic pathway will have to compete with each other for the limited supply of Coenzyme A. Since steroid synthesis is obligatory, it becomes compelling to curtail other less urgent metabolic processes. The final clinical presentation will depend on which metabolic process is affected most. If, however, in a situation where an exogenous steroid is administered, making steroid synthesis no longer mandatory for the time being, the activities of the acetyl-Co A related to steroid synthesis will be temporarily withheld, making available Coenzyme A for other metabolic processes that are urgently in need of the participation of Coenzyme A. This will lead to a temporary relief of the symptoms of the pathological process, which actually represents a particular derangement of a certain metabolic process.

BRIEF SUMMARY OF THE INVENTION

The present invention relates to the use of, by conventional standard, a huge dose of pantothenic acid to enable the body to synthesize the optimum level of steroids. The administration of pantothenic acid or a derivative thereof which is converted to pantothenic acid has the effect of imparting a sense of well-being to an individual and at the same time producing an anabolic effect in the body with subsequent increase in physical strength, resulting in improvement of athletic performance and exercise tolerance. During this process, because the natural balance of the various androgens is not disturbed, no side effect is observed. The dosage varies greatly with different individuals, but is estimated to be in the broad range of 20 mg to 20 gm per day, both on a short term and a long term basis.

The invention further relates to the administration of pantothenic acid to allow the body to synthesize the optimum amount of steroids the body will need and at the same time to have enough of pantothenic acid in the form of Coenzyme A to satisfy all other metabolic processes that may require the participation of Coenzyme A, thus treating the basic pathological processes of the clinical conditions that show improvement with empirical steroid treatment.

DEFINITIONS

The term "pantothenic acid" as used herein is intended to include not only pantothenic acid but any derivative thereof which is converted to pantothenic acid in the body.

DETAILED DESCRIPTION OF THE INVENTION

An object of the present invention is to enable an individual to achieve an improvement in the sense of well-being and in the physical strength resulting in an improvement of the exercise tolerance and athletic performance by administering pantothenic acid as a dietary supplement.

Pantothenic acid is one of the B group of vitamins. It functions in the body as a component of Coenzyme A. Coenzyme A is active in the body as acetyl-Co A which is the building block of cholesterol and all the steroidal compounds. As explained in copending U.S. patent application Ser. No. 07/580,019 and U.S. Pat. No. 5,039,698, there is evidence to show that, in most people, there is a deficiency of pantothenic acid in the body. This deficiency can be mild, but very often, it can be very severe, as can be seen by the amount, which can be up to more than 1,000 times the daily amount that is recommended by the Food and Drug Administration, needed to correct the deficiency over a period of several months, as in the treatment of acne vulgaris. A deficiency in pantothenic acid will necessarily reduce the level of acetyl-Co A in the body to below its optimum level. This will hamper the synthesis of the steroidal hormones, aside from the other functions. The androgens, the anabolic effect and the sense of well-being relating to the androgens, will all be affected.

With an adequate replacement of pantothenic acid in the body, the whole situation is reversed. All aspects of the functions of Coenzyme A will be satisfied. This will mean that all the steroidal compounds will be at their optimum level, as determined by the auto-regulatory function of the body. The androgenic level will be at its optimum level. The anabolic effect will be at its optimum level, as well as the sense of well-being. But the main feature that distinguishes this form of management to its conventional administration of androgenic-anabolic steroids is the lack of any side effects. The side effects of the androgenic-anabolic steroids have been mentioned. Thanks to the finely tuned auto-regulatory function of the body, the ratio of the various androgens synthesized will be matched to suit the occasion. With more exercise and more practice, the steroids with predominantly anabolic effect will be in more demand, and the body will probably direct its synthesis towards that direction without producing androgens that have predominantly virilizing effects. And all this time, the delicately balanced homeostasis of the body is not disturbed, so that no side effect is produced.

This is probably true even in the female. Here, the ratio of the female steroidal hormones, the estrogens and the progesterones, to the male androgens is just the reverse as in the male, with the female hormones making up the majority of the sex hormones. However, even with this minor proportion of androgens in the body, the body can still manage to synthesize enough anabolic steroids, when properly stimulated with exercise, to increase the muscle bulk and to improve the physical strength without producing any masculinizing and virilizing effect.

Pantothenic acid is a natural food, a vitamin that is essential to the well-being of the human species. So that, even if it is taken in large quantities, quantities much larger than is recommended by the Food and Drug Administration, there are no known side effects. This is true with even very prolonged administration. On the other hand, administration of the synthetic androgenic-anabolic steroids, even on a short term basis, is worrying, not to mention the side effect on prolonged administration and with a high dosage level.

Another object of the present invention is to provide a method whereby pantothenic acid or a derivative thereof which is converted to pantothenic acid in the body as a substitute for steroids which are used for medium and log term treatment of various clinical diseases. This substitute not only retains all the usefulness of the steroids, it also avoids all the undesirable effects that chronic steroid therapy may carry.

There is a sound theoretical basis for this. The steroids have two characteristics that are of particular interest with reference to the present context. Firstly, it is essential to life. Secondly, the steroids are not stored in the body, the amount that is stored in the adrenal cortex where steroids are synthesized is perhaps enough to maintain the body for a few minutes. For these two reasons, it is necessary for the body to synthesize steroids almost continuously. It is known that the steroids are synthesized from units of acetate in the form of acetyl-Co A, and because of their vital importance in the body, their synthesis overrides almost any other functions in the body. For this reason, in situations where there is a deficiency in Coenzyme A, many of the biochemical reactions requiring the participation of Coenzyme A will be curtailed, but not for steroid therapy. That is why, for deficiency state in Coenzyme A, Addisonian features do not arise; the body will continue to synthesize steroids as long as the cells synthesizing steroids are working. This is in contrast to patients suffering from Addison's Disease where there is a deficiency in steroid output. But this deficiency in steroid output is not due to a deficiency in Coenzyme A, but rather, to a deficiency in the synthesis operation, e.g., when the adrenal cortex of both adrenals is destroyed by pathological processes, and no adrenal cortex is left for steroid synthesis.

Coenzyme A is perhaps the most important coenzyme in the body because it plays a key role in the biosynthesis of many different lipids, including fatty acids, triacylglycerols and other complex lipids, prostaglandins, and cholesterol from which the steroid hormones are derived. That is why a deficiency in Coenzyme A will affect extensively the biochemical reactions in the body. When this occurs, the various metabolic processes and reactions that will require the participation of Coenzyme A will compete with each other, with the more important functions that are vital for the survival of the individual naturally gaining the preference. The body naturally will have a system of its own in determining the priority of the various biochemical reactions, with the less important reactions curtailed more in preference to the more important reactions, which are curtailed less. This is probably not the only criteria for determining the final direction of the biochemical reactions. Biochemical reactions have to follow the physical chemistry law of concentration, and it is the availability and concentration of other coenzymes in the tissue that will determine the final direction of the biochemical reaction. The other coenzymes are largely served by the other members of the B group of vitamins. That is possibly why the relative deficiencies in the other members of the B group of vitamins together with a deficiency in pantothenic acid will determine the final outcome of the clinical picture of pantothenic acid deficiency. And this probably is the reason why the clinical presentation of pantothenic deficiency, a reflection of the wide application of steroid therapy, can vary so much.

Since the steroids are vital for the immediate survival of the individual, their synthesis will not be curtailed to any significant extent even if there is a gross deficiency in Coenzyme A. In the body, there are probably other biochemical reactions in other tissues that are equally important to life, such as the brain tissue and the heart muscles, and these, too, are not easily sacrificed. However, biochemical reactions in maintaining the wear and tear of less important organs which are not essential for the immediate survival, such as joints, tendons, connective tissues, skin, etc. are not as fortunate. When there is a deficiency in Coenzyme A, their activities are curtailed drastically and disproportionately as compared to other more important organs. These organs, in a way, are losers in the battle of competitive inhibition, and their activities are inhibited, leading to common clinical manifestations in these tissues. This theory in fact correlates very well with clinical observation. Many of the disease processes that are benefitted by chronic steroid administration are diseases involving the tissues that are not essential for the immediate survival of the individual, such as the connective tissues and joints and tendons. Typically, the deficiency in pantothenic acid develops very slowly because of the wide distribution of the vitamin in food, and this is reflected in the slow progress of the disease processes.

It is also interesting to note that many of these diseases affect the female more than the male. Hitherto, this is not explained. But here again, with this theory in mind, it is easily explained. As explained in copending patent application Ser. No. 07/580,019, the absolute amount of sex hormones synthesized is a lot more in the female than in the male because of the large amount of progesterones synthesized during the luteal phase of the menstrual cycle, not to mention the sky-high progesterone levels during pregnancy. And sex hormone synthesis, like steroid synthesis, requires a lot of Coenzyme A. So that, in the female, throughout the adult years with incessant menstrual cycles, more Coenzyme A is used up towards that end, making a chronic deficiency in Coenzyme A more likely. That is why the connective tissue diseases, rheumatoid arthritis, rheumatism, etc. are much more common in the female than in the male.

It is to be noted that the deficiency in Coenzyme A always develops very slowly, over a relatively long period of time. Pantothenic acid, the only component of Coenzyme A that is likely to be deficient, is present in all tissues. This is to be expected, considering its positioning in the crossroad of the final common metabolic pathway. Regardless of the type of food one takes, it is always included in the diet. The only trouble is that the requirements of pantothenic acid are quite different for different individuals, for various reasons, including biochemical individuality. It is likely that most of us, if not all, are deficient in pantothenic acid, though the degree of deficiency may be quite different. This can account for the various clinical presentations, from symptomless to a wide range of disease entities, depending on probably the type of concommitant deficiencies in other coenzymes in other enzyme systems and other factors. In any case, the onset of these disease processes is always very gradual. In most cases, the biochemical changes and structural changes will take a long time to develop, in terms of months and years. So that, to reverse the situation with replacement with an adequate amount of pantothenic acid will not happen overnight. The biochemical changes, and in particular, the structural changes, will take a long time, if ever, to get back to normal.

The advantage of this form of substitution therapy with pantothenic acid to replace steroids in conditions that will be benefitted by chronic steroid therapy is obvious. Not only are all the side effects of steroid therapy completely avoided, but that the treatment has all the theoretical basis of treating the basic pathological processes. Whereas with steroid treatment, because of the serious side effects, the treatment is reserved as a last resort, and even then, the treatment has to be carefully monitored, with the dosage always kept to the minimum, and the duration the shortest possible. With this replacement therapy with pantothenic acid, there are no side effects to worry about. The initiation of the treatment no longer needs to wait till all other treatments have failed. Quite the contrary, the treatment can be put right to the very front line of defense. Since the treatment is directed right at the root of the pathology, the treatment has the added advantage of being curative. This form of treatment is not only curative, but preventive if a liberal amount of pantothenic acid is recommended to all very early on in life.

Pantothenic acid can be administered orally, intramuscularly, intravenously, rectally or topically. It is most conveniently administered orally in capsule form. Although the dosage amount of pantothenic acid can vary widely, a convenient capsule size contains 400 mg pantothenic acid as a pure powder. It can be dissolved in water for intramuscular or intravenous administration. Benzyl alcohol (10 mg) may be added for indolence.

Pantothenic acid can be admixed with a suitable carrier such as macrogols to make suppositories which can be administered rectally. One example of a suppository composition is 30% Macrogol 6000, 20% Macrogol 1540 and the balance pantothenic acid. A two gram suppository may contain 1 gram pantothenic acid. For topical use, a dermatologically acceptable vehicle may contain 30% emulsifying ointment, 0.1% chlorocresol and the balance water. Topical creams may contain up to 33% pantothenic acid. For ocular administration, a conventional vehicle useful for ocular administration may be used.

As indicated earlier, to achieve therapeutic effects in accordance with the present invention, pantothenic acid is administered in daily dosages of 0.02 to 20 grams. The exact dosage will vary with the condition treated, the method of administration, and the age and condition of the patient.

EXPERIMENTAL EXAMPLE 1

A controlled trial with 10 young male athletes in the age range of 17 and 18 was conducted. These 10 athletes were arbitrarily divided into 2 groups, 5 in each group. Their performance in the track event of 400 meters was studied. They were all high school students with regular training in mid-distance running, but were mediocre runners with their record in the 400 meters lying in the range of 57–59 seconds. They all had not bettered their own record in the previous 6 months. Both groups were asked to carry on their previous diet, but one group was given pantothenic acid in the form of calcium D-pantothenate. The pantothenate was given in the form of a thin syrup at a dosage of 10 gm per day in 4 divided doses. The pantothenate administration was continued for 3 months. At the start of the experiment, the time of the 400-meter event was timed for every runner. At the end of 3 months, the time of the same event was taken again. Whereas with the control group, the time on average improved 0.2 second from 58.5 to 58.3 seconds, the group that was fed 10 gm per day of pantothenic acid improved their time by exactly 3 seconds from 58.4 seconds to 55.4 seconds. This is a very significant improvement which cannot be ignored. The students in this group also claimed that they felt better after taking the pantothenic acid, and were not as tired as before, during training as well as attending classes in school.

EXPERIMENTAL EXAMPLE 2

The performance of 5 female high school athletes in the age range of 17–18 in the track event of 400 meters was studied. The situation was similar to that in Experimental Example 1. These were mediocre athletes with regular training. They were on ordinary diet. They had no improvement on their performance in the previous 6 months. They were given 10 gm of pantothenic acid per day in 4 divided doses for a period of 3 months. Before the experiment started, the performance in the event was timed. The time for the 400 meter event was in the range of 64.5–65.5 seconds with a mean of 65.1 seconds. At the end of 3 months, their performance was timed again. There was an improvement on the average of 2.8 seconds. The masculinizing and virilizing effects of the androgenic-anabolic steroids were completely absent. The menstrual cycles were not disturbed. Here again, a sense of well-being was observed, and they did not get tired easily, both in attending classes and in the practice sessions, as they did before the pantothenic acid was taken.

EXPERIMENTAL EXAMPLE 3

Pantothenic acid was given to 15 male individuals in the age range of 40–70 in a broad dose range of 20 mg to 20 gm per day, nd the effects on the sense of well being and exercise tolerance were observed. The study was continued for 3 months. They were all initially given a small dose of 20 mg per day. While there was one individual who could sense an improvement of well-being on that small dosage after 2 weeks of treatment, all the rest was not certain of any improvement until the dosage was increased to 500 mg per day. However, the sense of well-being and an increase in exercise tolerance became very obvious for everyone undergoing the experiment when the dose was raised to 5 gm a day, and after administering the pantothenic acid for more than 2 weeks. For the majority, this improvement seemed to be directly proportional to the dosage increase, with the improvement leveling off at different dosage level for different individuals. A few individuals seemed to improve progressively until the dosage was increased to 15-20 gm per day when further improvement was not observed. (There were no formal tests for the increase in exercise tolerance, but the individuals were asked to note the effort or the effortlessness when walking up a slope or on walking up flights of stairs.)

Incidentally, the sexual prowess of these male individuals was questioned. On theoretical grounds, with an increase of androgens in the body after administering of pantothenic acid, the sexual prowess should also improve. However, this is not observed. It may be related to the fact that 3 months is too short a period to achieve this effect. A much longer period of study probably will be required. Another reason is that sexual prowess is difficult to define, and in any case, is affected by a great number of other factors, psychological factors included.

EXPERIMENTAL EXAMPLE 4

Ten individuals, 2 males and 8 females, all in their 40's, complained of chronic rheumatic pain in their back, neck, shoulders, and the limbs for various duration of 2 to 10 years' duration. Investigations failed to pinpoint any pathology. They have to take analgesics from time to time to relieve the rheumatic pain. These patients were given pantothenic acid, in the form of syrup in the dose of 10 gm. per day in 4 divided doses. Initially, they were asked to continue their usual analgesics as required of the condition. Mild subjective improvement was noted by some after 2 to 3 weeks of treatment. However, over a period of months, at least 2 to 3 months, there began definite and noticeable changes in the degree of pain experienced, aside from the general improvement of well-being. The frequency that necessitates the intake of analgesics obviously decreased, and the dosage that is required to relieve the pain also decreased. The treatment was continued for one year and longer, the 2 males and 6 of the females had their pain completely relieved, with the 2 remaining females also having their pain relieved more than 80%. The 8 that had their pain relieved were put on a maintenance dose of 2 gm. per day, with no recurrence of the pain. The 2 that still had the pain were maintained on 10 gm. per day, with the symptom of pain getting better and better.

EXPERIMENTAL EXAMPLE 5

Three cases of established rheumatoid arthritis with more than 5 years of history in each case, all females and all in their forties, were studied. All had swollen finger joints with a definite deformity in one subject. They were all given 10 gm. of pantothenic acid per day in 4 divided doses. They were asked to continue their own analgesics whenever there were symptoms of pain. There was a definite decrease of stiffness and pain in the joints after three months. There was little change in the swelling and deformity of the finger joints. After six months, the need to administer analgesic became very occasional, and all three patients agreed that the symptoms must have improved by more than 80%. The pantothenic acid was continued for another six months until the symptoms of pain and discomfort had almost completely disappeared, although in one case, the pain never subsided completely and is still receiving 10 gm of pantothenic acid per day. The other two were put on a maintenance dose of 2 gm per day.

Here, it is interesting to note that Barton-Wright and Elliott (*Lancet*, 1963, 2, 862) described a temporary improvement in patients with rheumatoid arthritis when treated with daily intramuscular injection of 50 mg. of calcium-d-pantothenate, continued for four weeks. This improvement was associated with an increase in serum level of pantothenic acid. In another study, the General Practitioner Research Group (*Practitioner*, 1980, 224, 208) demonstrated no overall benefits in patients with various forms of arthritis when treated with 2 gm. of calcium pantothenate daily for eight weeks. But analysis of the results showed highly significant effects in reducing symptoms in patients with rheumatoid arthritis. In both studies, the dosage was too small and the period of treatment too short. Had the studies been repeated with a much larger dosage and a much longer period, the result might be entirely different.

EXPERIMENTAL EXAMPLE 6

Three cases of chronic bronchial asthma of more than ten years' history, two females in their forties and one male in his early seventies were studied. All had frequent asthmatic attacks and were all on various combinations of bronchodilators. They were given 10 gm. of pantothenic acid per day in four divided doses. They were asked to continue their bronchodilators. After two months of therapy with pantothenic acid, there was obvious improvement in the general well-being, with the exercise tolerance also noticeably improved. The asthmatic attacks were noticeably getting fewer and milder. When there was definite improvement, the dosage of the bronchodilators was reduced gradually over a period of several months. After six months, the dosage was essentially reduced to one-third of the original dosage, but the patients were feeling well with only very occasional and mild attacks. The treatment was carried on for another six months when in all three cases the bronchodilators were able to be discontinued without any further attacks of asthma. These patients were put on maintenance dosage of 2 gm. a day.

EXPERIMENTAL EXAMPLE 7

Two cases of allergic rhinitis of more than ten years of history were studied. Both had severe sneezing and running nose in the morning. Both are males in their forties. They were given 10 gm. per day of pantothenic acid in 4 divided doses. Over a period of four to six months, the severity of the symptoms were gradually reduced, and as the pantothenic acid was continued for another six months, somewhere in between that period, the symptoms became unnoticeable. A maintenance dose of 2 gm. a day was given.

EXPERIMENTAL EXAMPLE 8

One case of connective tissue disease was studied: a female aged 30 with disseminated lupus erythematosus presenting with rashes and itchy skin. She was put on steroid and chloroquine. After three months, the patient was put on 10 gm. of pantothenic acid per day, in four divided doses in addition to the steroid and chloroquine. The steroid and chloroquine were tailed off over a period of six months, and the improvement of the disease process, as a general impression, was much better than was expected of the disease process in general. The patient was given a maintenance dose of 5 gm. a day.

EXPERIMENTAL EXAMPLE 9

Three cases of chronic neurodermatitis of two to three years' duration were studied: two females and one male, all in their early twenties. All had steroid cream application on and off as a form of symptomatic treatment. The patients were given 20% pantothenic acid in a neutral cream base. The patients were asked to apply the cream to the affected area five to six times a day. In a matter of a few weeks, there was obvious improvement of the skin conditions.

No attempt was made to include all conditions that are benefitted by chronic steroid treatment for this form of substitution therapy with pantothenic acid. However, based on the strong theoretical ground, and the existing clinical results, there is little reason to believe that similar treatment with pantothenic acid in other disease processes benefitted by steroid therapy and local steroid application to be otherwise.

In view of the clinical results and the strong theoretical background for this form of substitution therapy with pantothenic acid to replace steroid in clinical medicine, it seems that a much smaller dosage of pantothenic acid will also help, e.g., 0.5 to 1 gm. a day, provided the treatment period is very much prolonged, and the initial response can be expected to develop very slowly. And as a preventive measure, by recommending pantothenic acid to all very early on in life, the dosage probably can be even smaller, but this depends on the biochemical variability of the individual and other factors.

It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

What is claimed is:

1. A method for treating a human being suffering from chronic bronchial asthma, acute rhinitis, disseminated lupus erythematosus or neurodermatitis which comprises administering to said human being a therapeutically effective amount of pantothenic acid or a derivative thereof which is converted to pantothenic acid in the body.

2. The method of claim 1 wherein said therapeutically-effective amount of said pantothenic acid or said derivative thereof is about 2 to 20 grams per day.

3. The method of claim 2 wherein said pantothenic acid or said derivative thereof administered orally, intravenously, intramuscularly or rectally.

4. The method of claim 3 wherein said pantothenic acid or said derivative thereof is administered orally in divided doses 4 or 5 times per day.

5. The method of claim 1 wherein said derivative of pantothenic acid is a salt of pantothenic acid.

6. The method of claim 5 wherein said salt of pantothenic acid is calcium D-pantothenate.

7. A method for treating a human being suffering from chronic bronchial asthma, acute rhinitis, disseminated lupus erythematosus, or neurodermatitis which comprises administering to said human being about 2 to 20 grams of pantothenic acid or calcium d-pantothenate orally in divided doses 4 or 5 times per day.

* * * * *